(12) United States Patent
Bogstad et al.

(10) Patent No.: US 7,752,888 B2
(45) Date of Patent: Jul. 13, 2010

(54) SYSTEM FOR GAS PERMEATION TESTING

(75) Inventors: David A. Bogstad, Perrysburg, OH (US); Daniel L. Witham, Holland, OH (US)

(73) Assignee: Plastic Technologies, Inc., Holland, OH (US)

( * ) Notice: Subject to any disclaimer, the term of this patent is extended or adjusted under 35 U.S.C. 154(b) by 46 days.

(21) Appl. No.: 11/575,459

(22) PCT Filed: Sep. 29, 2006

(86) PCT No.: PCT/US2006/038226

§ 371 (c)(1), (2), (4) Date: Mar. 16, 2007

(87) PCT Pub. No.: WO2007/041385

PCT Pub. Date: Apr. 12, 2007

(65) Prior Publication Data

US 2009/0229347 A1  Sep. 17, 2009

Related U.S. Application Data

(60) Provisional application No. 60/722,278, filed on Sep. 30, 2005.

(51) Int. Cl. *G01N 15/08* (2006.01)
(52) U.S. Cl. ............................................. 73/38; 73/37
(58) Field of Classification Search ............... 73/37, 73/38, 40, 40.5 R, 52
See application file for complete search history.

(56) References Cited

U.S. PATENT DOCUMENTS

| | | | | |
|---|---|---|---|---|
| 3,248,930 A | * | 5/1966 | Speegle et al. | 73/38 |
| 3,348,395 A | * | 10/1967 | Orr, Jr. et al. | 73/38 |
| 3,494,175 A | * | 2/1970 | Cusick et al. | 73/37 |
| 3,590,634 A | * | 7/1971 | Pasternak et al. | 374/54 |
| 3,729,983 A | * | 5/1973 | Coppens | 73/40.7 |
| 3,751,973 A | * | 8/1973 | Strauss et al. | 73/45 |
| 3,805,593 A | * | 4/1974 | Sandoz et al. | 73/49.2 |
| 3,805,594 A | * | 4/1974 | Hayashi | 73/49.2 |
| 3,850,040 A | | 11/1974 | Orr, Jr. et al. | |
| 4,459,843 A | * | 7/1984 | Durham | 73/37 |
| 4,511,044 A | * | 4/1985 | Connor et al. | 209/522 |
| 4,747,298 A | * | 5/1988 | McDaniel | 73/49.3 |
| 4,788,850 A | * | 12/1988 | Buschor et al. | 73/49.2 |
| 4,914,810 A | * | 4/1990 | Zohler | 73/38 |
| 5,001,935 A | * | 3/1991 | Tekkanat et al. | 73/799 |
| 6,013,026 A | * | 1/2000 | Krauter et al. | 600/193 |
| 6,591,661 B2 | * | 7/2003 | Davey | 73/38 |
| 6,598,463 B2 | * | 7/2003 | Sharp et al. | 73/38 |

(Continued)

FOREIGN PATENT DOCUMENTS

| | | | |
|---|---|---|---|
| FR | 2 308 100 | | 11/1976 |
| JP | 10267826 A | * | 10/1998 |
| JP | 2002310843 A | * | 10/2002 |
| JP | 2004279281 A | * | 10/2004 |
| WO | WO 0148452 A2 | * | 7/2001 |
| WO | WO 2005052555 A1 | * | 6/2005 |
| WO | WO 2007077335 A1 | * | 7/2007 |

*Primary Examiner*—David A. Rogers
(74) *Attorney, Agent, or Firm*—Fraser Clemens Martin & Miller LLC; Donald R. Fraser

(57) ABSTRACT

A system for measuring gas permeation through container walls is disclosed, wherein a pressure fluid is introduced into a container to be tested. Once the pressure fluid is introduced into the container, the pressure fluid is drawn out of the container and tested to determine the permeation characteristics of the container.

11 Claims, 4 Drawing Sheets

U.S. PATENT DOCUMENTS

| | | | |
|---|---|---|---|
| 6,817,238 B2 * | 11/2004 | Go Boncan et al. | 73/149 |
| 6,857,307 B2 * | 2/2005 | Gebele et al. | 73/38 |
| 6,964,191 B1 | 11/2005 | Tata | |
| 6,964,197 B2 * | 11/2005 | Davis et al. | 73/700 |
| 7,059,175 B2 * | 6/2006 | Volfkovich et al. | 73/38 |
| 2004/0040372 A1 * | 3/2004 | Plester et al. | 73/38 |
| 2005/0118365 A1 * | 6/2005 | Miyazaki et al. | 428/34.1 |
| 2007/0215046 A1 * | 9/2007 | Lupke et al. | 118/712 |

\* cited by examiner

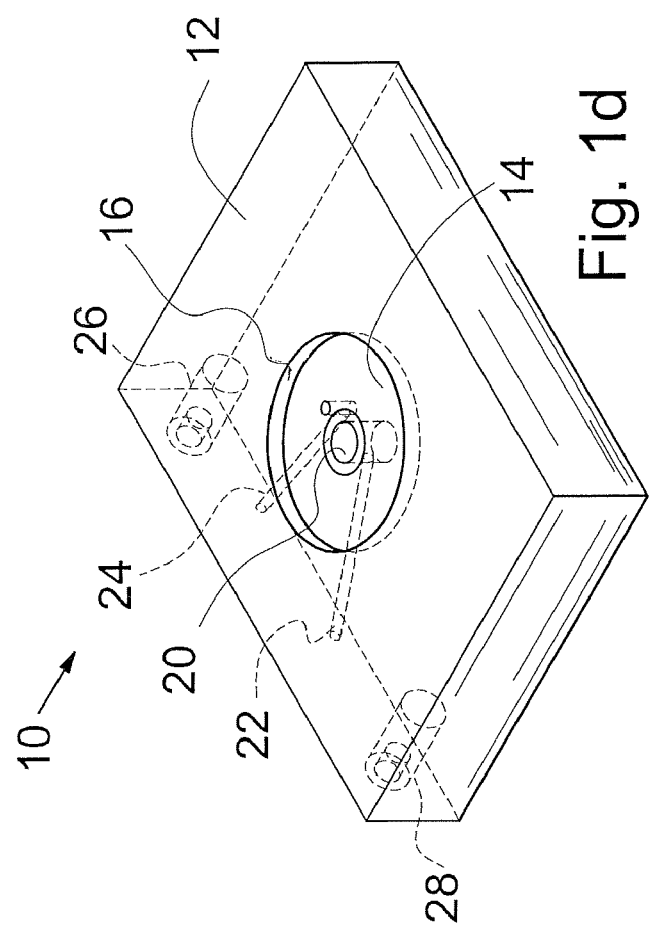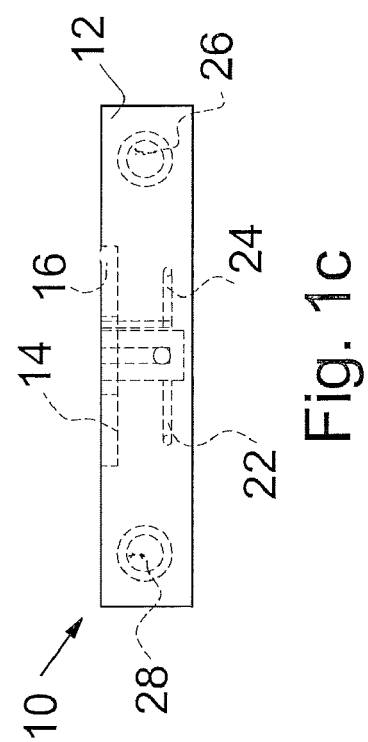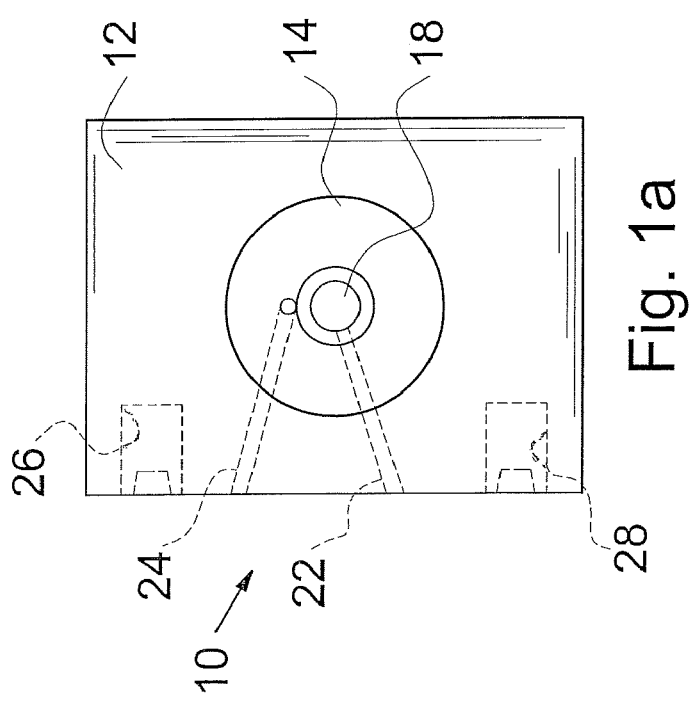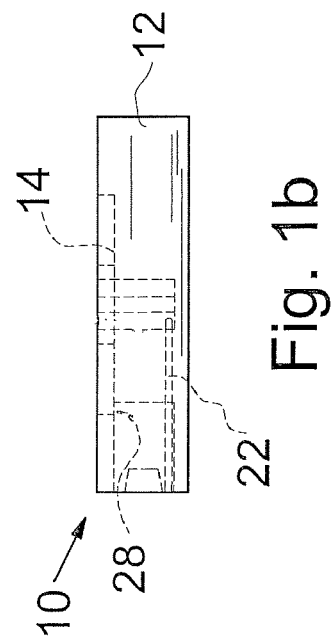

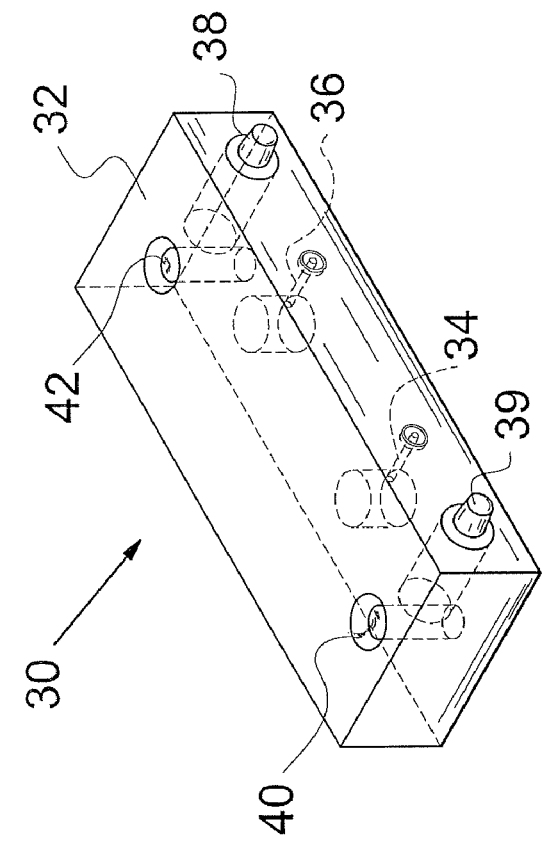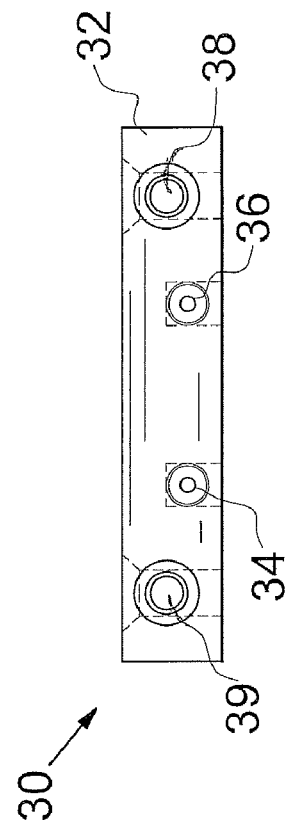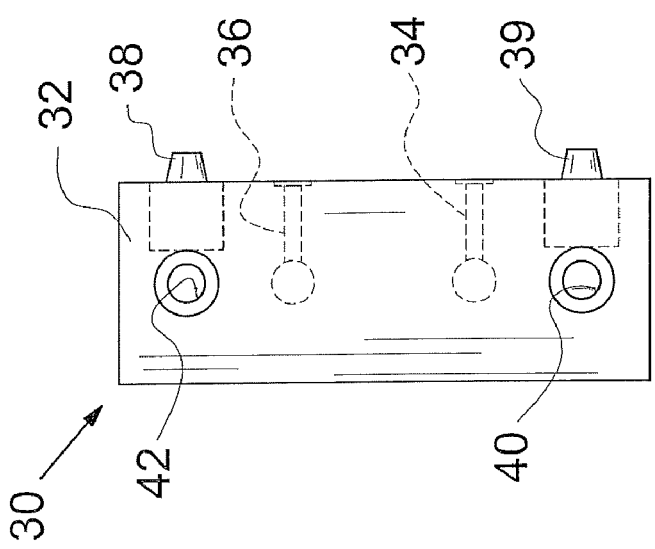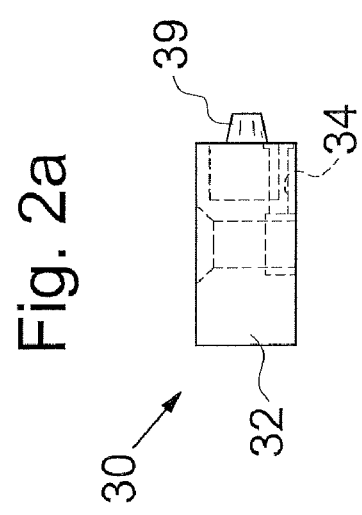

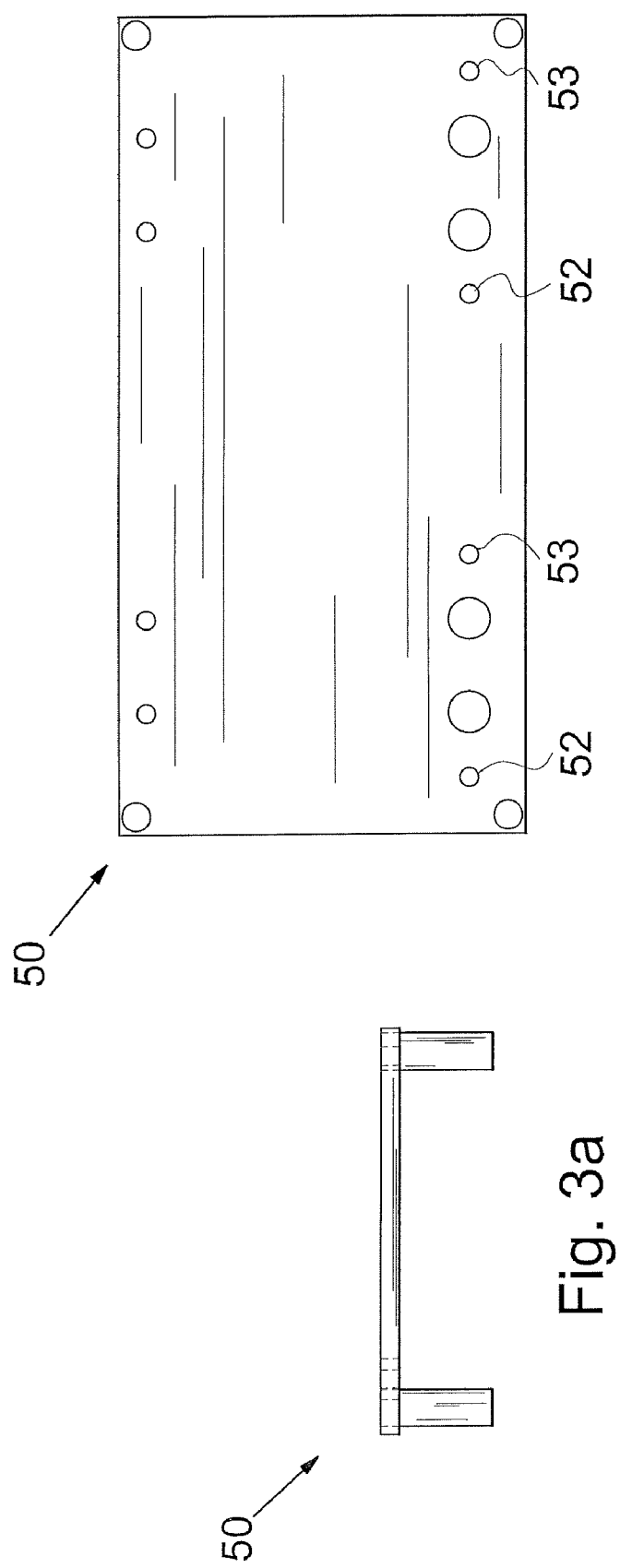
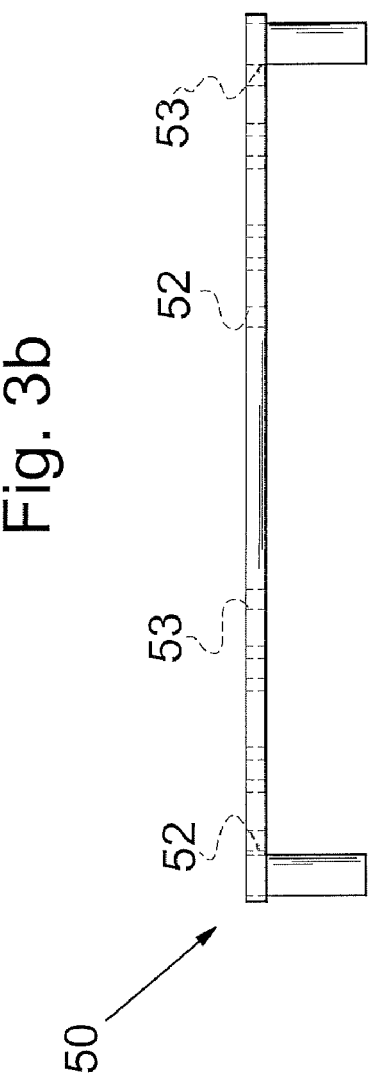
Fig. 3a
Fig. 3b
Fig. 3c

SYSTEM FOR GAS PERMEATION TESTING

CROSS-REFERENCE TO RELATED APPLICATION

This application claims the benefit of U.S. Provisional Patent Application Ser. No. 60/722,278 filed on Sep. 30, 2005.

BACKGROUND OF THE INVENTION

1. Field of the Invention

The present invention relates to a container testing apparatus. More particularly, the present invention relates to a system for measuring gas permeation through plastic container walls.

2. Description of the Prior Art

In the preservation of beverages which are liable to be affected by oxidation, there is a problem that the beverages are oxidized by a small amount of oxygen present in a container used for storage. Therefore, it is of paramount importance to ascertain the oxygen permeation characteristics of the plastic containers to be used for the beverage storage. In the prior art, the systems for testing oxygen permeation require that each time a container is placed on or removed from a system for gas permeation testing, the containers to be tested must be affixed onto flat plates which have soldered connections that must be screwed onto a mating fitting of an associated manifold. Frequently, testing errors result, primarily from minute leakage around the fittings and components. Problems further increase with repeated use of the fittings.

One solution is to replace the fittings more often and to more meticulously affix the container to the flat plates to ensure a better connection. However, these options significantly increase the amount of time between testing of containers while still allowing for testing errors.

Those skilled in the art have continued to search for the solution of how to provide a practical testing system.

SUMMARY OF THE INVENTION

In order to solve the problem longstanding in the art, a simplified and improved system for mounting and connecting materials and containers for permeation testing has been surprisingly provided.

In one embodiment of the present invention, the system is constructed of two main components; namely, moveable sample plates to which the containers are affixed, and a permanently mounted manifold.

The aforementioned sample plate is provided with three components; namely, a support for a container to be tested; conduits through which a gas may flow; and bushings to ensure proper alignment of the sample plate with the manifold.

The manifold is provided with three components; namely, pins to ensure proper alignment with the bushings of the sample plate; conduits through which a gas may flow to and from the container during testing; and grooves around the conduits which retain seals.

It is an object of the present invention to produce a system for measuring gas permeation through a plastic material of the type employed for producing plastic containers.

It is a further object of the present invention to eliminate screw-type tubing connections from the system to allow for faster removal and exchange of samples for testing.

It is still a further object still a further object of the present invention to decrease the time required to conduct the testing procedures.

Still another object another object of the invention is to improve the reliability of the seal between the sample plate and container by constructing a mounting plate with a pocket that the container fits into before being attached with a suitable adhesive material.

Further objects and advantages of the invention will be apparent from the following description and appended claims, reference being made to the accompanying drawings forming a part of the specification.

BRIEF DESCRIPTION OF THE DRAWINGS

Other objects and advantages of the invention will become readily apparent to those skilled in the art from reading the following description of the invention when considered in the light of the accompanying drawings, in which:

FIGS. 1a, 1b, 1c, and 1d are, respectively, top plan, end elevational, front elevational, and perspective views of a sample plate embodying the features of the invention;

FIGS. 2a, 2b, 2c, and 2d are, respectively, top plan, end elevational, front elevational, and perspective views of a manifold embodying the features of the invention; and FIGS. 3a, 3b, 3c, and 3d are, respectively, end elevational, top plan, and front elevational views of a base plate embodying the features of the invention.

Figure 4:
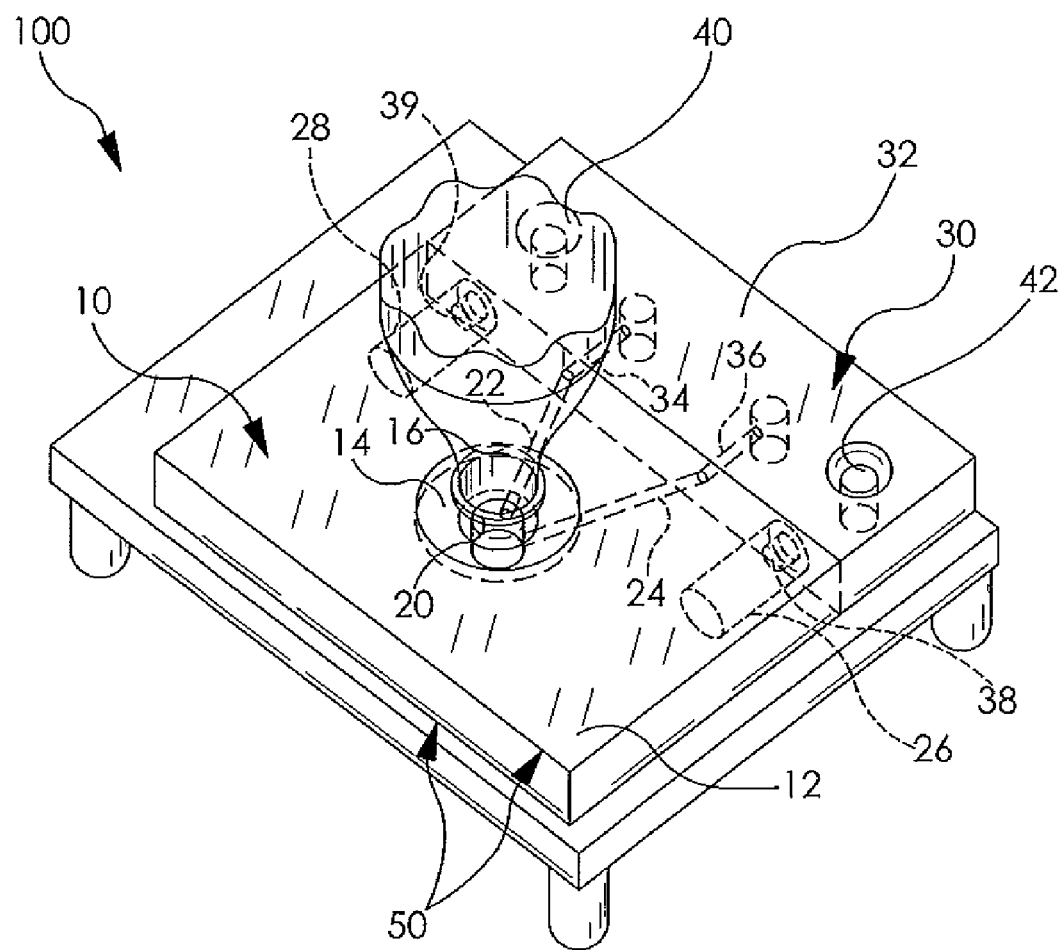
FIG. 4 is a perspective view of a gas permeation system having a container to be tested thereon according to an embodiment of the invention.

It is to be understood that the present invention is not limited in its application to the details of construction and arrangement of parts illustrated in the accompanying drawings, since the invention is capable of other embodiments, and of being practiced or carried out in various ways within the scope of the appended claims. Also, it is to be understood that the phraseology and terminology employed herein is for the purpose of description, and not of limitation.

DETAILED DESCRIPTION OF THE PREFERRED EMBODIMENT

Referring to the accompanying drawings, there is shown components of a system for mounting and connecting plastic material, such as used in containers for permeation testing which embody the features of the invention.

The system includes two main components; namely, moveable sample plates to which a container to be tested is affixed; and an associated manifold system.

A bushing shown in FIG. 1d is adapted to receive pins of an associated manifold 30 shown in FIG. 2d. The elements may be suitably affixed to the base plate 50 shown in FIGS. 3a, 3b, and 3c by threaded fasteners, for example.

The sample plate 10 comprises a main body 12 having an annular recess 14 for receiving the neck or finish of a plastic container to be tested. The recess 14 is defined by an annular shoulder 16. A coaxial recess 18 is formed centrally of the annular shoulder 16. The open end of the recess 18 is defined by an upstanding annular 20. A conduit 22 is formed in the main body 12 to provide communication between a source of pressure fluid and the interior of the container being tested.

Another conduit 24 is formed in the main body 12 to provide communication with a return of the pressure fluid introduced through the conduit 22. A pair of spaced apart bushings 26, 28 is formed to extend inwardly of the main body 12 and receive cooperating locating pins, as will be explained hereinafter.

FIGS. 2a, 2b, 2c, and 2d illustrate a manifold 30 which comprises a main body 32 having at least one conduit 34 to communicate with the inlet of the sample plate conduit 22 and a conduit 36 communicating with the sample plate conduit 24, and coupling means including pins 38, 39 for selectively coupling the sample plate 10 and the manifold 30.

Grooves may be circumscribed around the inlets and outlets of conduits of the sample plate 10 and the manifold 30 to retain seals. The seals are utilized to close the system when the sample plate 10 is in operative position. The grooves circumscribed around the conduits are preferably grooves adapted to retain o-ring seals.

Any suitable means of selectively coupling the sample plate 10 and manifold 30 may be used. It has been found that satisfactory results may be achieved by utilizing the spaced apart inwardly extending bushing 26, 28 in the sample plate 10 to receive the corresponding respective pins 38, 39 of the manifold 30. Manifold mold-style pins 38, 39 as shown in FIG. 2d ensure proper alignment with sample plate mold-style bushings 26, 28 as shown in FIG. 1d.

The manifold 30 can be mounted to a base plate 50 as illustrated in FIGS. 3a, 3b, and 3c. The base plate 50 serves as a support for the entire system. The manifold 30 is provided with spaced apart passageways or holes 40, 42 to receive suitable threaded fasteners. The threaded ends of such fasteners are threadably received within internally threaded holes 52, 53, respectively of the base plate 50 to assure proper alignment. A pair of spaced apart passageways or holes is formed in the base plate 50 to allow the passage of conduits communicating with the manifold conduits 34, 36. In the embodiment illustrated, the base plate 50 is adapted to accommodate a pair of manifolds 30. The pair of manifolds may be formed separately or may be formed as one integral unit. The sample plates 10 which are used with the pair of manifolds 30 may also be formed separately or as one integral unit.

Once aligned, the sample plate 10 is connected with the manifold 30, as shown in FIG. 4. The connection may be tightened to urge the sample plate 10 against o-rings in the manifold 30. Compression of the sample plate 10 against the o-rings closes the conduit-container-manifold system.

The sample plate 10, manifold 30, and base plate 50 are preferably constructed of aluminum or other lightweight durable alloy. Lightweight components are desired for easier portability of system components and to allow rapid exchange of sample plates during testing. However, the components of the system may be constructed of any appropriate material that withstand system temperature, pressure, and use requirements.

The testing of a container typically involves the following steps. First, a container is placed on and secured to the mounting area of a sample plate 10 with an epoxy resin or other suitable adhesive material. As shown in FIG. 4, the sample plate 10 is selectively coupled to the manifold 30 which is already attached to the base plate 50. The sample plate 10 is securely compressed against the o-rings of the manifold 30 to close the system. Compression occurs by tightening the connection between the sample plate 10 and the manifold 30 by any means, such as by clamping, for example.

Once the system is closed, the pressure fluid is allowed to flow through into the container through the manifold conduit 34 and the sample plate conduit 22. Favorable results have been found wherein the pressure fluid is pure nitrogen. Once the pressure fluid is introduced into the container, it flows out of the container through the sample plate conduit 24 and the manifold conduit 36. Any gas which permeated through the container will also flow out of the container through the sample plate conduit 24 and the manifold conduit 36 to the testing sensor.

A system described above for testing a container may also be used to test permeation characteristics of other materials, such as a film for example. In this situation, the film is disposed on an open-ended container (not shown) and sealed or otherwise connected to the container so the flow of fluid around the film into the container is militated against. The sample plate conduits 22, 24 described above are in communication with the container. The pressure fluid is introduced into the container and exposed to the inner side of the film. The outer side of the film is exposed to atmosphere or a controlled environment. Gas which permeates through the film is picked up by the pressure fluid and tested to determine the permeation characteristics of the film.

In accordance with the provisions of the patent statutes, the present invention has been described in what is considered to represent its preferred embodiment. However, it should be understood that the invention can be practiced otherwise than as specifically illustrated and described without departing from its spirit or scope.

What is claimed is:

1. A system for gas permeation testing of a sample material comprising:
   a manifold having a body, the body having a first manifold conduit formed therein in fluid communication with a source of pressure fluid and a second manifold conduit formed therein in fluid communication with a testing sensor; and
   a sample plate for receiving a sample material, said sample plate being selectively attached to said manifold, said sample plate having a first conduit formed therein in fluid communication with the first manifold conduit providing fluid communication between the source of pressure fluid and an interior of the container and a second conduit formed therein in fluid communication with the second manifold conduit providing fluid communication between the interior of the container and the testing sensor.

2. The system for gas permeation testing in accordance with claim 1, wherein said manifold is adapted to be removably mounted to a base plate.

3. The system for gas permeation testing in accordance with claim 1, wherein the sample material is a plastic container.

4. The system for gas permeation testing in accordance with claim 3, wherein said sample plate includes at least one recess formed thereon for receiving the container to be tested.

5. The system for gas permeation testing in accordance with claim 4, further including an adhesive disposed in the recess adapted to secure the container thereto.

6. The system for gas permeation testing in accordance with claim 5, wherein the adhesive is an epoxy resin.

7. The system for gas permeation testing in accordance with claim 1, wherein said manifold includes a pair of spaced apart pins which are received by a pair of spaced apart bushings formed in said sample plate.

8. The system for gas permeation testing in accordance with claim 7, wherein a groove adapted to receive a seal is formed around each of the spaced apart pins.

9. The system for gas permeation testing in accordance with claim 8, wherein the seal is an o-ring.

10. The system for gas permeation testing in accordance with claim 7, wherein a groove adapted to receive a seal is formed around each of the spaced apart bushings.

11. The system for gas permeation testing in accordance with claim 10, wherein the seal is an o-ring.

* * * * *